United States Patent [19]
Black et al.

[11] Patent Number: 5,306,917
[45] Date of Patent: Apr. 26, 1994

[54] ELECTRO-OPTICAL SYSTEM FOR MEASURING AND ANALYZING ACCUMULATED SHORT-WAVE AND LONG-WAVE ULTRAVIOLET RADIATION EXPOSURE

[75] Inventors: Michael Black, Foster City; Vladimir Kupershmidt, Pleasanton; Michael Spitkovsky, Sunnyvale, all of Calif.

[73] Assignee: Reliant Laser Corporation, Foster City, Calif.

[21] Appl. No.: 928,918

[22] Filed: Aug. 12, 1992

[51] Int. Cl.$^5$ .............................................. G01J 1/44
[52] U.S. Cl. ................................................ 250/372
[58] Field of Search .................................. 250/372 EM

[56] References Cited

U.S. PATENT DOCUMENTS

| | | | |
|---|---|---|---|
| 4,010,372 | 3/1977 | Adler et al. | 250/372 EM |
| 4,428,050 | 1/1984 | Pellegrino et al. | 250/372 EM |
| 4,535,244 | 8/1985 | Burnham | 250/372 EM |
| 5,008,548 | 4/1991 | Gat | 250/372 EM |
| 5,151,600 | 9/1992 | Black | 250/372 EM |
| 5,173,609 | 12/1992 | Lacoste et al. | 250/370.07 |

FOREIGN PATENT DOCUMENTS

| | | | |
|---|---|---|---|
| 262425 | 10/1989 | Japan | 250/372 EM |
| 2236182 | 3/1991 | United Kingdom | 250/372 EM |

*Primary Examiner*—Carolyn E. Fields

[57] ABSTRACT

An electro-optical system intended for medical use that measures and analyses an individual's cumulative short-wave and long-wave UV-radiation exposure as detected by sensor 10 of the system attached to the individual. Sensor 10 separately registers sequences of UV-A and UV-B signals which are synchronized in time by clock pulses. After a predetermined interval sensor 10 is connected to an analyzer unit 12 that statistically processes the collected data to derive risk factor and generate predictive information. Such information permits the physician to predict individual-specific levels of ultraviolet (UV) radiation potentially harmful to the skin and help protect the individual from skin cancer and similar diseases with solar radiation causation.

14 Claims, 5 Drawing Sheets

ELECTRO-OPTICAL SYSTEM FOR MEASURING AND ANALYZING ACCUMULATED SHORT-WAVE AND LONG-WAVE ULTRAVIOLET RADIATION EXPOSURE

BACKGROUND

1. Field of the Invention

The present invention relates to the field of medical diagnostic systems, particularly to a system for determining and predicting individual skin-damaging levels of ultraviolet (UV) radiation.

2. Description of Prior Art

Solar radiation reaching the earth consists of electromagnetic energy ranging from ultraviolet (UV) radiation to infrared (IR) radiation. UV radiation is further subdivided into three types: UV-A, UV-B, and UV-C. UV-C radiation are those wavelengths in the range of 200 to 285 nanometers (nm); it is totally absorbed by the earth's atmosphere. UV-B, from about 285 to 318 nm, is known to cause skin cancer in humans. UV-A, from about 315 to 400 nm, is mostly responsible for tanning. However, UV-A has also been found to play a role in skin cancer and is the cause of eye cataracts, solar retinitis, and corneal dystrophies.

In view of the latest problems associated with global warming and development of holes in the ozone layer of the earth atmosphere, the risk of development of skin cancer and other diseases caused by intensified exposure to solar radiation is greatly increasing.

Based on general principles and techniques for radiometry and photometry, several UV radiation-measuring and warning instruments have been developed and made commercially available.

A personal UV radiometer, described in U.S. Pat. No. 5,008,548 to Nahum Gat, 1991, includes an LCD display, a photocell, and an integrated circuit for processing user inputs and UV radiation data.

However, this device of U.S. Pat. No. 5,008,548 does not take into account the changes in skin pigmentation which occur while a person is being exposed to solar radiation. Furthermore, this device is not convenient, since it is intended for attachment to an article of clothing and may restrict movement of a subject during rigorous physical activity, for instance, a volleyball game.

An apparatus, disclosed in U.S. Pat. No. 4,985,632 to Frank Bianco et al., 1991, comprises an electronic wristwatch having a digital readout for displaying the time, the day, and the month. It also incorporates a photodiode for detecting skin-damaging UV radiation, a microcomputer, and four function buttons.

This device, however, is not user-friendly due to its large number of functions, many of which are superfluous. Moreover, like the radiometer, the wristwatch does not take into account skin pigmentation changes which occur during exposure to UV radiation. Furthermore, it cannot monitor UV radiation when placed in the shade.

Furthermore, all of the above prior-art devices are based on the assumption that the amount of UV radiation that may be safely tolerated by human skin is independent of the rate at which such incident radiation is accumulated. These prior art devices measure only the cumulative magnitude of incident UV radiation, and do not factor any rate measurements into the determination of a safe UV-radiation threshold.

In other words, if one of two identical cumulative UV-radiation doses is an intense dose received relatively quickly and the other a longer-duration exposure of lesser intensity, none of the prior-art devices are able to distinguish between these two doses with respect to relative differences in potential harmful effect on the skin. The prior-art devices cannot monitor differences in UV-radiation exposure rates.

The concept of total accumulated UV radiation as the single measure of the effect on human skin of exposure to UV radiation is flawed in principle for two major reasons. Firstly, as embodied in the prior-art devices, the cumulative dose that is monitored does not differentiate between the two most important constituent spectral ranges within the overall UV-radiation spectrum: UV-A and UV-B. These constituent UV-radiation spectra each have specific and differing effects on human tissue ranging from the propagation of skin cancer to cataract formation. Therefore, each of these spectral ranges deserves separate monitoring, data collection and analysis.

Secondly, as discussed above, data on cumulative dosage only without consideration of UV-exposure rates, i.e., the intensity of incident UV-radiation reaching the detector per unit time, cannot properly distinguish between harmful and unharmful UV exposures. The practice of measuring only accumulated UV radiation stems from the use of the Geiger counter for measuring radioactive dosage. The measurement of cumulative radioactivity received by a human body is a proper measurement because the harmful effect of radioactivity on human tissue is, in fact, a cumulative one: no matter what the rate of exposure, once the maximum cumulative threshold of exposure is reached, the damage is irreversibly done.

However, such is not the case with accumulated solar radiation. Solar radiation can be accumulated in large doses without harm if the dose is accumulated over a sufficiently long period of time. Equivalent cumulative dosages might be received in one day or one month. In the first case, the dose could be dangerous, whereas in the second case it might be completely benign. Therefore, data collected only for cumulative radiation exposure is neither indicative of actual skin damage done, nor predictive with respect to future harmful effects on the tissue.

To initiate a solution to these problems of effective UV radiation monitoring and analysis, the inventors submitting the present application developed a special noseshade for monitoring both cumulative UV-A and UV-B radiation exposure. This noseshade is fully described in U.S. patent application Ser. No. 867,433 filed Apr. 13, 1992, now U.S. Pat. No. 5,151,600. However, the noseshade is not intended for the analysis of recorded data, not does it interface to a radiation exposure analyzer.

OBJECTS AND ADVANTAGES

It is accordingly an object of the invention to provide an improved system for selectively measuring UV-A and UV-B radiation doses and for measuring variations in an individual's exposure times to UV-radiation. Other objects are to provide a system for analyzing the radiation dosage data obtained from the individual, determine an actual skin cancer risk factor associated with the individual's exposure to different types of UV radiation, and selectively measure the UV-radiation exposure of the face and body of the individual, or of the individual's face only.

Other advantages and features of the invention will become apparent from a consideration of the ensuing description and drawings.

BRIEF DESCRIPTION OF DRAWINGS

A general perspective view of the system of the invention is shown in FIG. 1.

FIGS. 5 and 6 are graphs which show variation of ultraviolet-A and ultraviolet-B intensities in time, respectively.

REFERENCE NUMERALS USED IN THE DRAWINGS AND DESCRIPTION

10—sensor
12—UV data analyzer
14—interface unit
15—output terminal
16, 18—photodetectors
20, 22—optical band-pass filters
24, 26—logarithmic amplifier
28, 30—voltage-to-frequency converter
32—microcontroller
34—multiplexer
35—peak radiation-intensity detector
36—CPU
38—RAM
40—ROM
42—EAROM
44—clock-signal generator
46—interface unit
47—input terminals
48—skin-protection-factor switch
49—slider
50—power switch
51—liquid crystal display
52—dry cell
53—pushbutton
54—casing
55—pushbutton
56—clip
70—controller
72—graphic-output unit
74—display unit
76—floppy-disk drive unit
78—CPU
80—ROM
82—RAM
84—subject data input unit
85—data input terminal

DETAILED DESCRIPTION OF THE APPARATUS OF THE INVENTION

Figure 1:
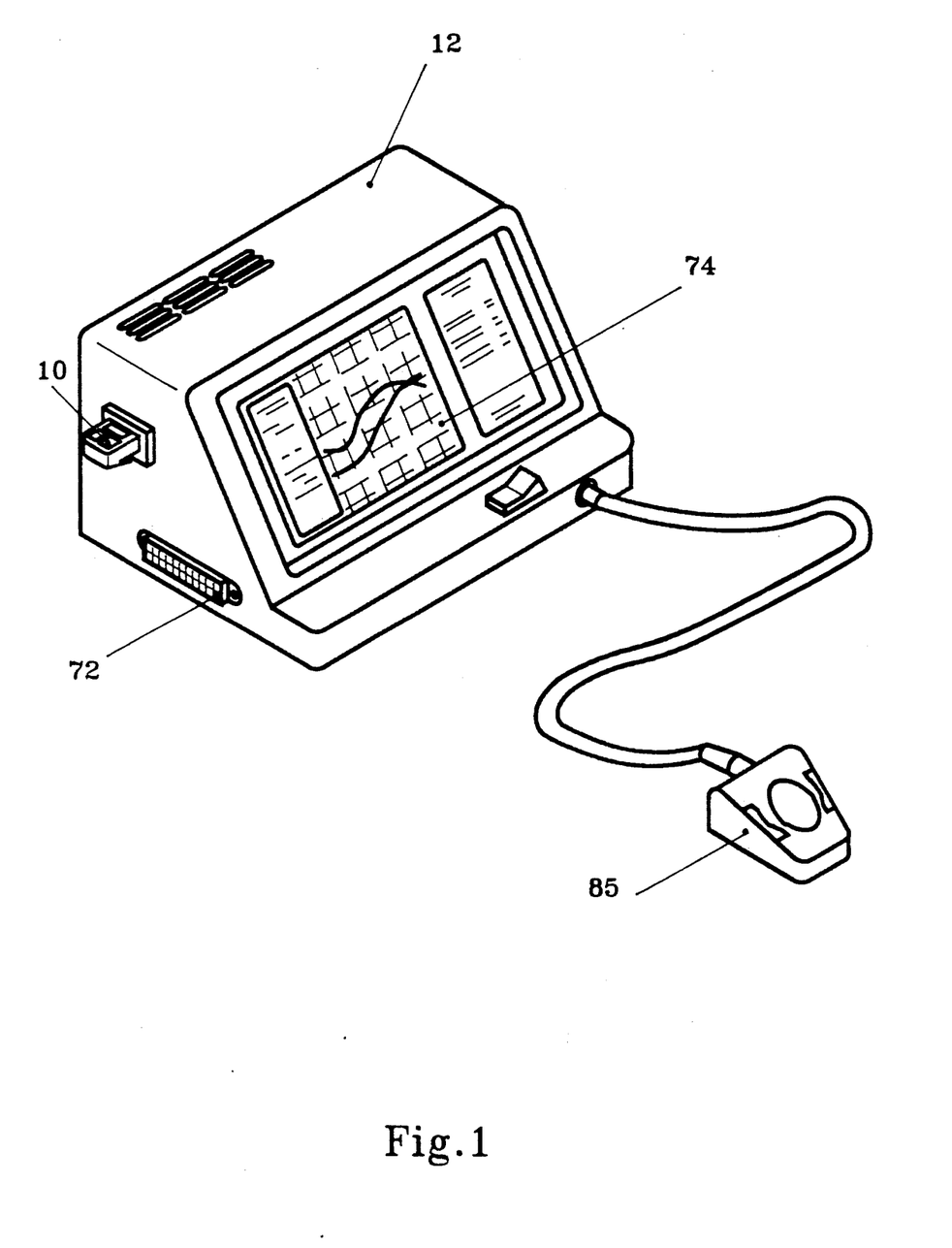

A general perspective view of the system of the invention is shown in FIG. 1. The system consists of two major parts, i.e., a sensor 10, which is carried by a subject whose UV-radiation exposure is to be measured, and a data analyzer 12 which may be located remotely from sensor 10, e.g., in a doctor's office who keeps personal files of the subjects. Data analyzer also has a built-in interface unit 14 for reading information from sensors. Data-analyzer interface has input terminals 47.

Each unit mentioned above will be further considered separately in detail.

Figure 2:
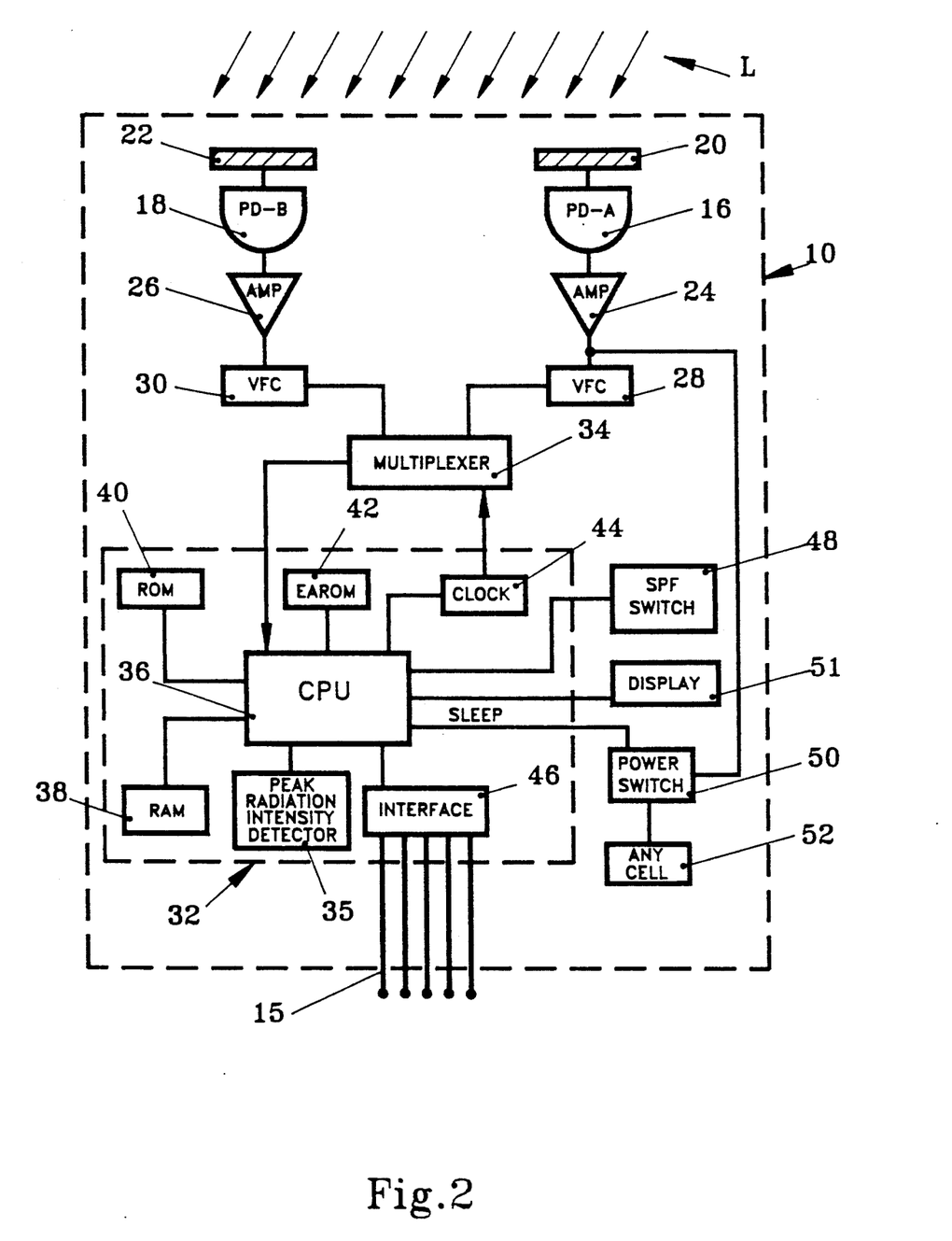
FIG. 2 is a schematic block-diagram of a sensor.

A schematic block-diagram of sensor 10 is shown in FIG. 2.

Two identical UV-enhanced photodetectors 16 and 18 are located at the input end of sensor 10. A sensitive area of each photodetector is covered by an optical band-pass filter. Photodetector 16 is covered by a filter 20 which transmits only a UV-A spectral range of incident solar radiation, while photodetector 18 is covered by a filter 22 which transmits both a UV-A and UV-B radiation.

Output ends of both photodetectors 16 and 18 are connected to logarithmic amplifiers 24 and 26, respectively. Logarithmic amplifiers, in turn, are connected to voltage-to-frequency converters (VFC) 28 and 30, respectively. Outputs of VFC 28 and 30 are electrically connected to a microcontroller 32 through a multiplexer 34.

Microcontroller 32 includes a central processing unit (CPU) 36, a random-access-memory (RAM) unit 38, and read-only-memory (ROM) unit 40. RAM 38 and ROM 40 are connected to CPU 36. Connected to CPU also are an electrically-alterable ROM 42, a interface unit 46, a clock-signal generator 44, and a peak-intensity switch 35. Interface unit has terminals 15 for connection to data-analyzer terminals 47. Peak radiation-intensity detector 35 determines the peak intensity of a signal in each time interval of data measurement. Peak radiation-intensity detector 35 also compares the peak intensity with a predetermined threshold and produces on its output an average value of the intensity and the peak value. Registration of the peak intensity value and the average value in predetermined intervals of time is carried out under the command of a program contained in ROM 40. This data is necessary for an appropriate correlation analysis. When sensor 10 is located in a shade or in a dark place, intensity signals will be equal to zero. Zero signals will not be memorized, but the magnitude of the latest recorded peak will remain in EAROM 42.

Located externally of microcontroller 32 are a skin-protection-factor (SPF) switch 48, a dry-cell power source 52 connected through a power switch 50, and a liquid-crystal display (LCD) 51.

Figure 3:
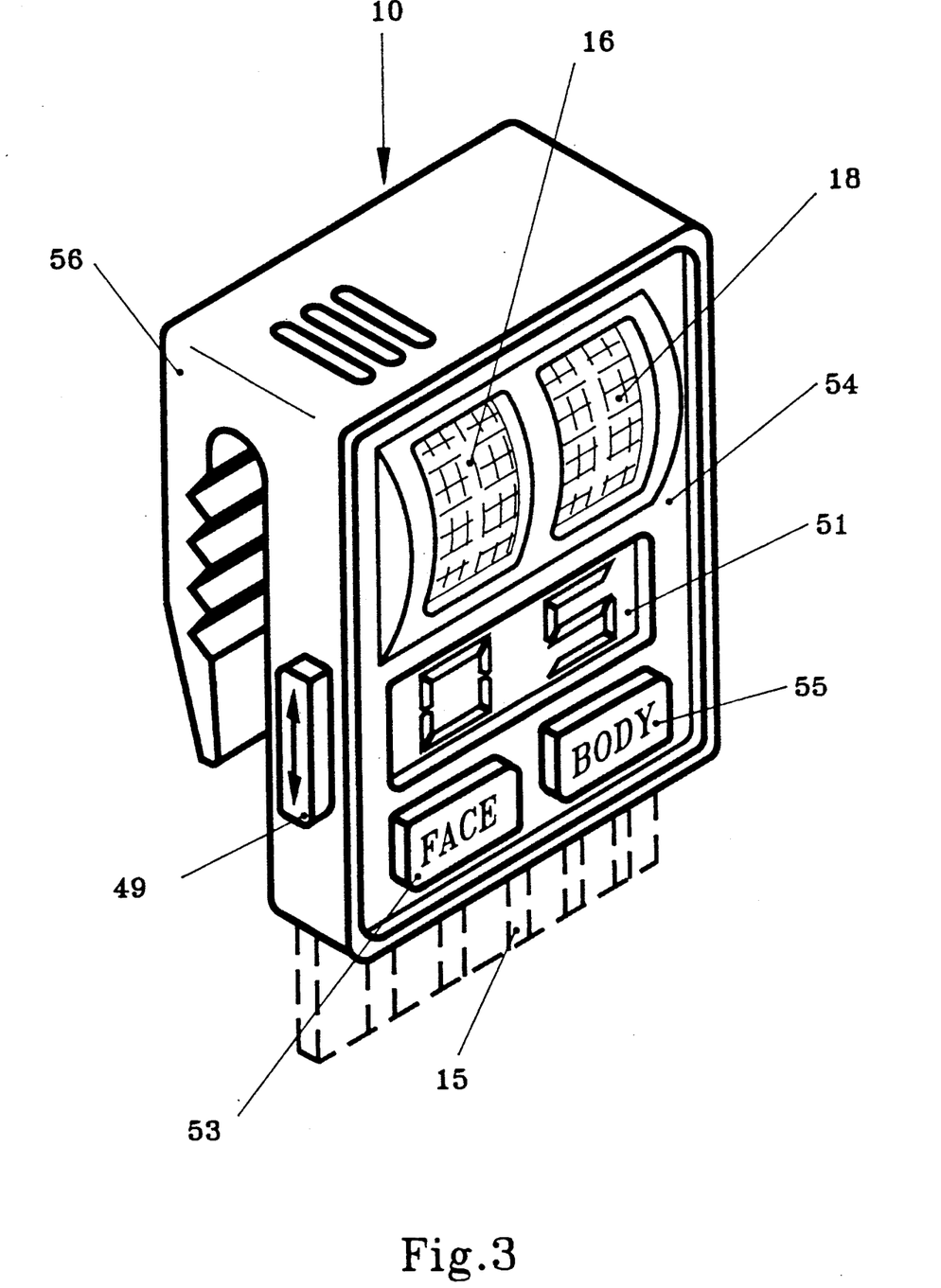
FIG. 3 is a three-dimensional external view of the sensor.

FIG. 3 is a perspective external view of sensor 10. The entire microcontroller is made in the form of a microchip (not shown) on the basis of IC manufacturing technique. The entire sensor 10 may be placed into a small casing 54 having dimensions of 2 to 3 cm$^2$. Casing 54 has a clip 56 for attachment of the sensor, e.g., to a conventional worn item such as a pair of sunglasses that will be exposed to solar radiation at the same time and in generally the same manner as will be the skin of the individual. Clip 56 may be used for attaching sensor to a breast pocket of a jacket (not shown) or to a swimming suit. Photodetectors 16 and 18 are located on the face side of sensor which also contains LCD 51. The bottom side of sensor 10 has output terminals L5 of the type similar to terminals of a telephone cord. Terminals 15 are intended for connection to interface 14.

The above-mentioned skin-protection factor is a number ranging from "1" to "99" that designate skin lotions. On the basis of the amount of UV-blocking ingredients contained in their formulae, the higher the number, i.e., the "skin protection factor", the greater the UV-blocking effect of the lotion. Such lotions are routinely used by individuals exposed to solar radiation.

Application of an appropriate lotion to some degree protects the skin. Therefore, the effect of the lotion must be taken into consideration for analysis since it may significantly change the output data of sensor 10. Lotions have up to two-digit numbers which are set on LCD 51. Since face lotions can differ in their protective action from those lotions purchased for application to other parts of the body, sensor 10 has two different inputs for both face and body lotions. These inputs are made via pushbutton 53 and 55. Pushbutton 53 is intended for inputting a face lotion number and pushbutton 55 enables a body lotion number input. Each depression of a pushbutton adds one number in ascending sequence to the digital readout shown on LCD 48. When dry-cell power source 52 is inserted into its working position, sensor 10 is automatically switched on for a continuous operation.

Pushbuttons 53 and 55 are synchronized with clock-signal generator 44 via CPU 36. Thus, when data is inputted through pushbuttons 53 or 55, microcontroller 32 memorizes the data-input time and the number of the lotion.

In order to protect output terminals 15 from damage and in order to prevent their interference with the face of the individual, these output terminals may be retractable into casing 54 of sensor 10. For this purpose, terminals 47 are connected to a slider 49 which is located on the outer side of casing 54 and is used for projecting or retracting output terminals 15.

Data analyzer 12 of the system is located remotely from sensor 10 and is intended for analyzing data obtained from sensor 10 when the latter is connected to analyzer 12 via interface 14 at predetermined intervals of time.

Figure 4:
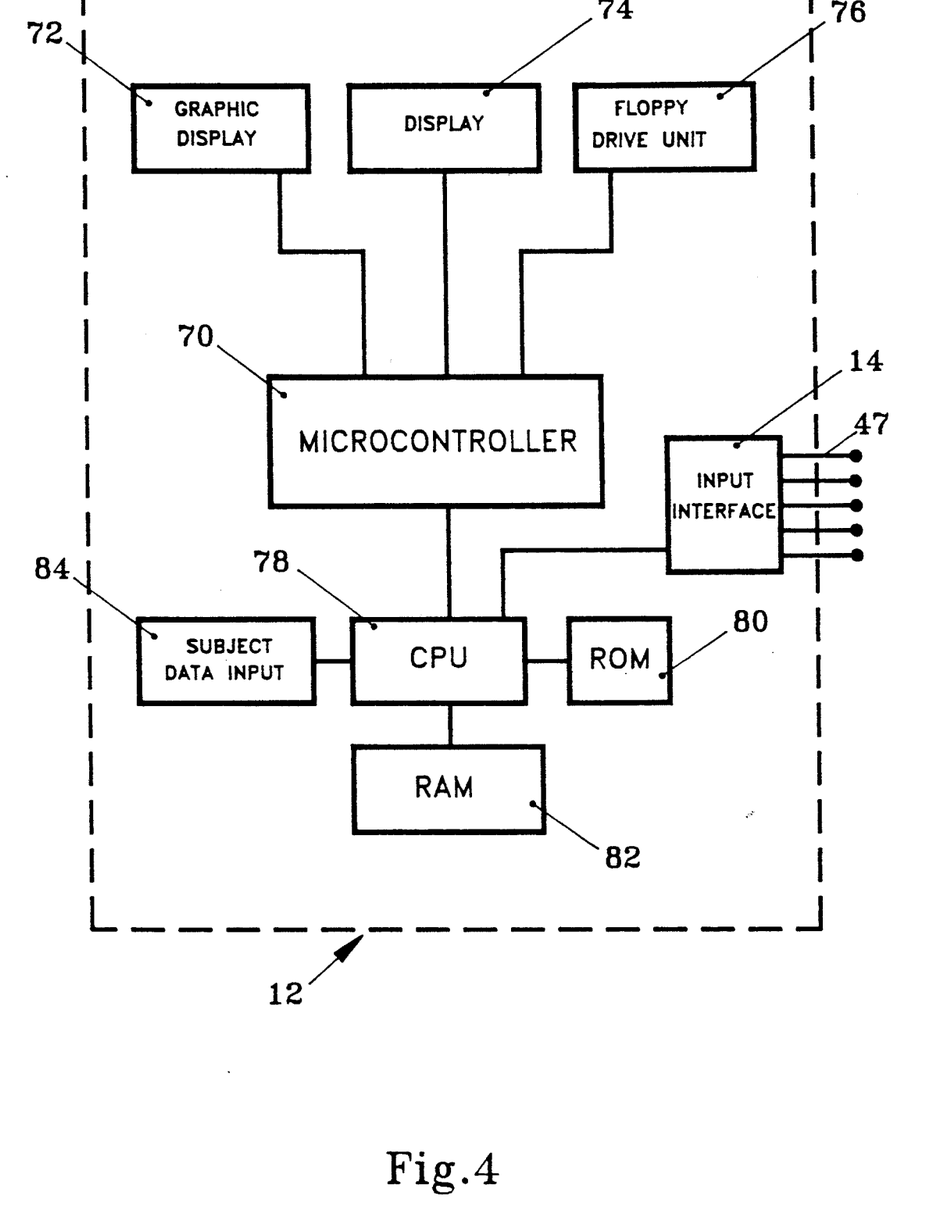
FIG. 4 is a block-diagram of the data analyzer.

FIG. 4 is a block-diagram of data analyzer 12. Data analyzer 12 has a controller 70 which is connected to a graphic output unit 72 which records output data on paper, e.g., a built-in thermal printer (not shown), a display unit 74, and a floppy disk drive unit 76 for recording the analyzed information to a floppy disk (not shown). Controller 70 is connected to CPU 78. The latter is connected to a ROM 80, a RAM 82, and a subject's data input unit 84. Subject's data input unit 84 has a data input terminal 85 through which personal data of the subject, such as age, monitoring starting date, patient's checking date, time of the season (spring, summer, etc.), skin type, etc., can be inputted into the analyzer.

Interface 14 also is connected to CPU 78.

ROM 80 of data analyzer 12 contains an algorithm intended for processing data obtained from sensor 10. This algorithm is based on statistical data concerning the occurrence of skin cancer and accompanying diseases caused by exposure to solar radiation.

OPERATION

For monitoring a UV-radiation exposure, the individual attaches sensor 10, e.g., to a conventional worn item such as a pair of sunglasses that will be exposed to solar radiation at the same time and in generally the same manner as will be the skin of the individual. Clip 56 may be used for attaching sensor to a breast pocket of a jacket (not shown) or to a swimming suit.

If the individual uses a skin-protection lotion(s), pushbutton 53 is depressed in order to enter the face lotion number, and pushbutton 55 for entering a body lotion number. In the majority of cases, however, only the face is exposed to solar radiation. Face-only exposure is analogous to the case of a body being coated with a protective lotion having a 100% reflectivity. Such a theoretical body lotion can be designated by a conventional two-digit number 99, which is entered by means of pushbutton 55. In this case, sensor 10 will be able to automatically register the lotion operation time.

Figure 5:
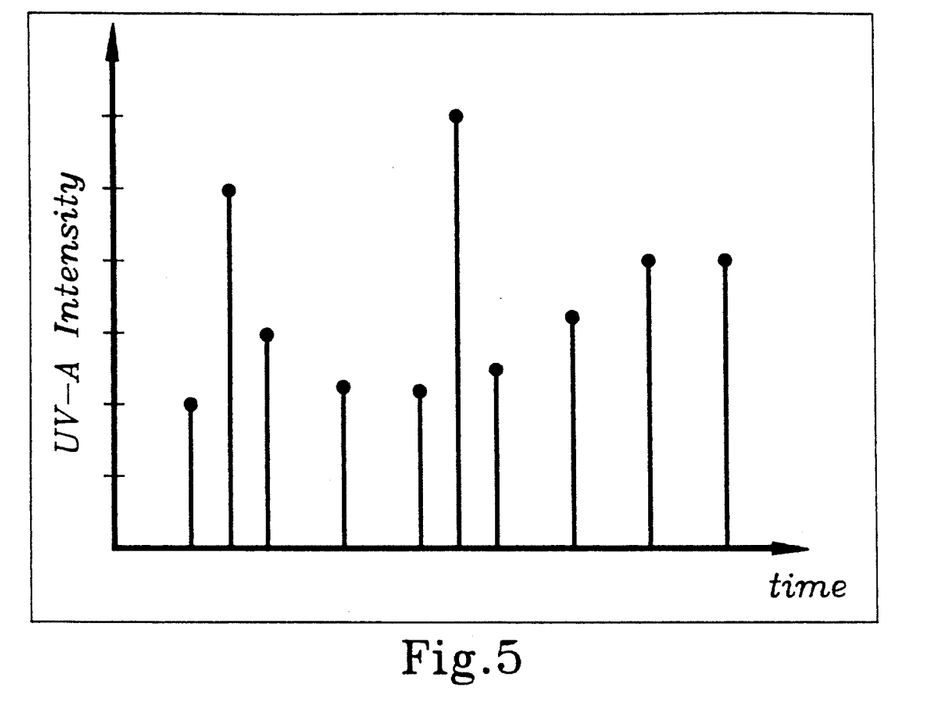
Figure 6:
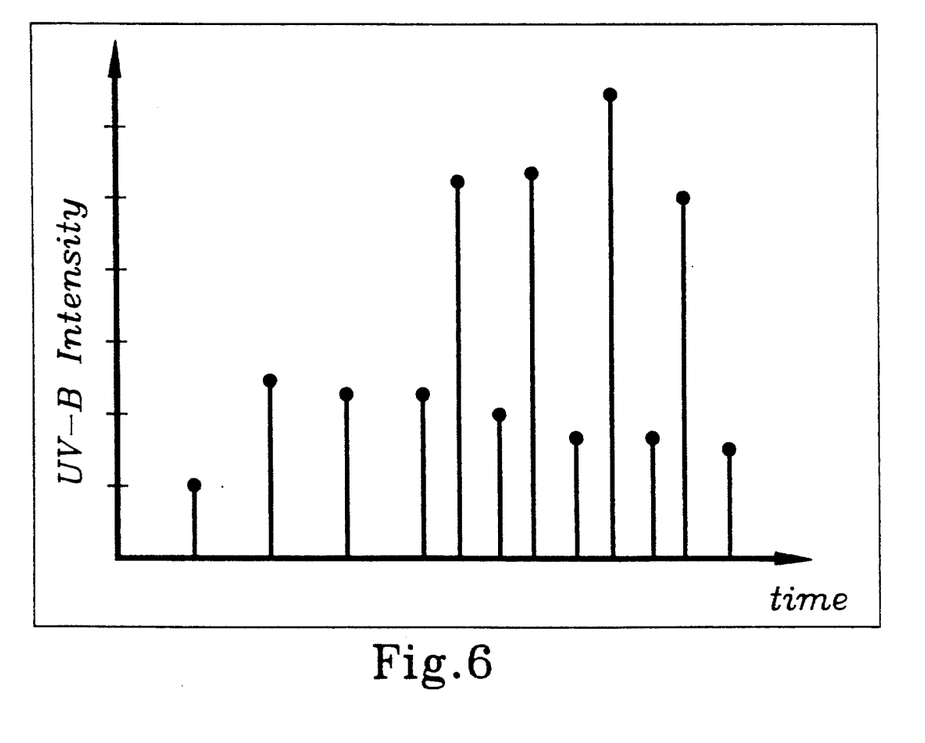

When sensor 10 is ON, the incident UV radiation enters through optical band-pass filters 20 and 22, UV-A and UV-B photodetectors 16 and 18, respectively. Output signal voltages of photodetectors 16 and 18 are amplified by logarithmic amplifiers 24 and 26, respectively. The amplified signals are converted by voltage-to-frequency converters 28 and 30 into frequency signals. Both frequency signals are sent to multiplexer 34 which transfers the signals sequentially to CPU 36 of microcontroller 32. The spectral-radiation intensity and time data obtained from each channel, i.e., UV-A radiation channel and UV-B radiation channel, is stored in EAROM 14. The data is registered at predetermined intervals, e.g., every 60 minutes. In the above-mentioned 60-minute interval, peak radiation-intensity defector 35 generates two output signals: a peak-intensity value, and an average-intensity value. Both these values are stored in EAROM 42. A graphical example of peak intensity in the UV-A and UV-B ranges is shown in FIGS. 5 and 6, where FIG. 5 is a UV-A range data and FIG. 6 is a UV-B range data. Intensities are plotted on the ordinate axis, and time is plotted on the abscissa axis.

After a predetermined period of time, e.g., three months, the wearer of sensor 10 may visit a doctor to check the accumulated data and obtain a recommendation. The physician may already maintain a patient file for this person.

UV-data analyzer 12 is located in the doctor's office. When the doctor receives sensor 10 with the individual cumulative UV-exposure data, he/she connects sensor 10 to interface unit 14 of analyzer 12 and reads out the data.

Upon connection of sensor 10 to interface unit 14, the output data of sensor is transferred to RAM 82 and to ROM 80 via CPU 78. Data are then recorded on floppy disk 76 and printed-out by graphic output unit 72.

Data obtained by analyzer 12 is analyzed by various statistical methods in order to derive a risk-factor. The data may be presented in various ways, such as a root-mean-square (RMS) dose, an average dose, and a peak dose along with the associated rates of exposure, etc.

SUMMARY, RAMIFICATIONS, SCOPE

Thus, it has been shown that the invention provides an improved system for selectively measuring UV-A and UV-B radiation doses and for measuring time intervals during which a monitored individual is exposed UV-radiation. The system makes it possible to obtain radiation dosage data, to determine an actual risk factor related to the degree of exposure to UV radiation, and to selectively measure exposures to UV-radiation of an individual's body, respectively.

Although the UV-radiation measurement and analysis system has been shown and described in the form of one specific embodiment, this embodiment, its parts, materials, and configurations have been given only as examples, and many other modifications of the system are possible. For example, sensor 10 may have a strip-like configuration. An adhesive tape can be used instead of an attachment clip. The data collected from UV-radiation monitoring can be processed by using various algorithms and methods of analysis.

Therefore, the scope of the invention should be determined, not by the example given, but by the appended claims and their legal equivalents.

What we claim is:

1. An electro-optical system for measuring and analyzing an individual's short-wave and long-wave ultraviolet radiation exposure, comprising:
   a housing and means for attaching said housing to an item carried or worn by said individual;
   a sensor located in said housing, said sensor having a ultraviolet-A photodetector and a ultraviolet-B photodetector, each photodetector having a sensitive area;
   said sensor comprising:
      a first bandpass filter covering said sensitive area of said ultraviolet-A photodetector and a second bandpass filter covering said sensitive area of said ultraviolet-B photodetector;
      a microcontroller for registering and storing output data from said ultraviolet-A photodetector and said ultraviolet-B photodetector;
      a power switch connected to an output of said microcontroller;
      a power source connected to said power switch;
      a plurality of output terminals on said sensor;
      a first logarithmic amplifier having an input connected to said ultraviolet-A photodetector and an output and a second logarithmic amplifier having an input connected to said ultraviolet-B photodetector and an output;
   a multiplexer having an input connected to said output of said first logarithmic amplifier via a first voltage-to-frequency converter and to said output of said second logarithmic amplifier via a second voltage-to-frequency converter, said multiplexer being connected to said microcontroller;
   a ultraviolet-data analyzer located remotely from said sensor and having a controller, a first central processing unit connected to said controller, and a plurality of analyzer output units; and
   an interface unit located on said analyzer, said interface unit having means for connecting said interface unit to said terminals of said sensor;
   said microcontroller further including:
      a second central processing unit;
      a clock generator for generating a clock signal, said clock generator being connected to said first central processing unit;
      a read-only-memory unit connected to said first central processing unit;
      a random-access-memory connected to said first central processing unit;
      an electrically alterable read-only memory connected to said first central processing unit;
      an interface connected to said second central processing unit; and
      a peak radiation-intensity detector connected to said first central processing unit, said peak radiation-intensity detector having means for registering peak radiation-intensity value and average radiation-intensity value in predetermined intervals of time.

2. The system of claim 1 wherein said sensor has a skin protection factor switch connected to said first central processing unit of said microcontroller.

3. The system of claim 2 wherein said skin protection factor switch has means for recording two-digit numbers of two different skin-protecting lotions, one of which is a face-skin lotion and another is a body-skin lotion.

4. The system of claim 3 wherein said means for recording skin-protecting lotion numbers comprises two pushbuttons and a two-digit liquid-crystal display connected to said pushbuttons.

5. The system of claim 1 wherein said plurality of analyzer output units comprise a graphic output unit, a display unit, and a floppy disk drive unit.

6. The system of claim 5 wherein said analyzer further includes a subject's data input unit connected to said central processing unit of said analyzer.

7. An electro-optical system for measuring and analyzing an individual's short-wave and long-wave ultraviolet radiation exposure, comprising:
   a housing and means for attaching said housing to an item carried or worn by said individual;
   a sensor located in said housing, said sensor having a ultraviolet-A photodetector and a ultraviolet-B photodetector, each photodetector having a sensitive area, said sensor having a plurality of output terminals;
   said sensor comprising:
      a first bandpass filter covering said sensitive area of said ultraviolet-A photodetector and a second bandpass filter covering said sensitive area of said ultraviolet-B photodetector;
      a microcontroller for registering and memorizing output data of said ultraviolet-A photodetector and said ultraviolet-B photodetector;
      a power switch connected to an output of said controller;
      a power source connected to said power switch; and said plurality of output terminals of said sensor;
      a first logarithmic amplifier having an input connected to said ultraviolet-A photodetector and an output and a second logarithmic amplifier having an input connected to said ultraviolet-B photodetector and an output; and
      a multiplexer having an input connected to said output of said first logarithmic amplifier via a first voltage-to-frequency converter and to said output of said second logarithmic amplifier via a second voltage-to-frequency converter, said multiplexer being connected to said microcontroller;
   a ultraviolet-data analyzer located remotely from said sensor and having a controller, a first central processing unit connected to said controller, and a plurality of analyzer output units; and
   an interface unit located on said analyzer, said interface unit having means for connecting said interface unit to said output terminals of said sensor;
   said microcontroller further including:
      a second central processing unit;
      a clock generator for generating a clock signal, said clock generator being connected to said first central processing unit;
      a read-only-memory unit connected to said first central processing unit;
      a random-access-memory connected to said first central processing unit;

an electrically alterable read-only memory connected to said first central processing unit;

a interface connected to said second central processing unit; and a peak radiation-intensity detector connected to said first central processing unit, said peak-radiation intensity detector having means for registering peak intensity value and average intensity value in predetermined intervals of time.

8. The system of claim 7 wherein said sensor has a skin protection factor switch connected to said central processing unit of said microcontroller, said skin protection factor switch having means for recording two-digit numbers of two different skin-protecting lotions, one of which is a face-skin lotion and another is a body-skin lotion.

9. The system of claim 8 wherein said means for recording skin-protecting lotion numbers comprises two pushbuttons and a two-digit liquid-crystal display connected to said pushbuttons.

10. The system of claim 7 wherein said analyzer output units comprise a graphic output unit, a display unit, and a floppy disk drive unit, said analyzer further including a subject's data input unit connected to said second central processing unit of said analyzer.

11. An electro-optical system for measuring and analyzing short-wave and long-wave ultraviolet radiation exposure of an individual, comprising:

a housing with an attachment means for attaching said housing to an item carried by said individual;

a sensor located in said housing having a ultraviolet-A photodetector and a ultraviolet-B photodetector, each photodetector having a sensitive area, said sensor having a plurality of output terminals;

said sensor comprising:

a first bandpass filter covering said sensitive area of said ultraviolet-A photodetector and a second bandpass filter covering said sensitive area of said ultraviolet-B photodetector;

a microcontroller for registering and memorizing output data of said ultraviolet-A photodetector and said ultraviolet-B photodetector;

a power switch connected to an output of said microcontroller;

a power source connected to said power switch and to said output terminals of said sensor;

a first logarithmic amplifier having an input connected to said ultraviolet-A photodetector and an output and a second logarithmic amplifier having an input connected to said ultraviolet-B photodetector and an output; and a multiplexer having an input connected to said output of said first logarithmic amplifier via a first voltage-to-frequency converter and to said output of said second logarithmic amplifier via a second voltage-to-frequency converter, said multiplexer being connected to said microcontroller;

a ultraviolet-data analyzer located remotely from said sensor and having a controller, a first central processing unit connected to said controller, and analyzer output units; and an interface unit located on said analyzer, said interface unit having means for connecting said interface unit to said output terminals of said sensor;

said microcontroller further including:

a first central processing unit;

a clock generator for generating a clock signal, said clock generator being connected to said first central processing unit;

a read-only-memory unit connected to said first central processing unit;

a random-access-memory connected to said first central processing unit;

an electrically alterable read-only memory connected to said first central processing unit;

an interface connected to said second central processing unit; and a peak radiation-intensity detector connected to said first central processing unit and having means for registering peak radiation-intensity value and average radiation-intensity value in predetermined intervals of time.

12. The system of claim 11 wherein said sensor has a skin protection factor switch connected to said first central processing unit of said microcontroller, said output terminals of said sensor being retractable into said housing of said sensor.

13. The system of claim 12 wherein said skin protection factor switch has means for recording two-digit numbers of two different skin-protecting lotions, one of which is a face-skin lotion and another is a body-skin lotion, said means for recording skin-protecting lotion numbers comprises two pushbuttons and a two-digit liquid-crystal display connected to said pushbuttons.

14. The system of claim 13 wherein said analyzer output units comprise a graphic output unit, a display unit, and a floppy disk drive unit, said analyzer further includes a subject's data input unit connected to said second central processing unit of said analyzer.

* * * * *